(12) United States Patent
Seelich et al.

(10) Patent No.: US 6,548,729 B1
(45) Date of Patent: Apr. 15, 2003

(54) FIBRIN SPONGE

(75) Inventors: Thomas Seelich, Vienna (AT); Edgar Scheel, Hagen (DE); Johann Odar, Mühlhausen (DE); Yves Alain Delmotte, Tertre (BE)

(73) Assignees: Baxter Aktiengesellschaft, Vienna (AT); Baxter International Inc., Deerfield, IL (US)

(*) Notice: Subject to any disclaimer, the term of this patent is extended or adjusted under 35 U.S.C. 154(b) by 0 days.

(21) Appl. No.: 09/451,361

(22) PCT Filed: Sep. 18, 1998

(86) PCT No.: PCT/EP98/05995

§ 371 (c)(1),
(2), (4) Date: May 26, 2000

(87) PCT Pub. No.: WO99/15209

PCT Pub. Date: Apr. 1, 1999

(30) Foreign Application Priority Data

Sep. 19, 1997 (AT) .............................................. 1593/97

(51) Int. Cl.⁷ ......................... A61F 13/00; A61K 38/00; C07K 14/00
(52) U.S. Cl. ............................ 602/48; 514/12; 514/21; 530/381; 530/389
(58) Field of Search ...................... 602/41–59; 604/304, 604/306; 514/12, 21; 530/381, 384

(56) References Cited

U.S. PATENT DOCUMENTS

| | | | |
|---|---|---|---|
| 4,606,337 A | | 8/1986 | Zimmermann et al. |
| 4,909,251 A | * | 3/1990 | Seelich ........................ 606/213 |
| 5,883,078 A | * | 3/1999 | Seelich et al. ................ 514/12 |
| 5,962,405 A | * | 10/1999 | Seelich ......................... 514/2 |
| 6,063,061 A | * | 5/2000 | Wallace et al. ............. 604/181 |

FOREIGN PATENT DOCUMENTS

| | | |
|---|---|---|
| EP | 0 131 740 A2 | 1/1985 |
| EP | 0 505 962 A1 | 3/1992 |
| EP | 0 485 210 A2 | 5/1992 |
| EP | 0 562 864 A1 | 9/1993 |
| WO | WO 96/03160 A1 | 2/1996 |
| WO | WO 96/17633 | 6/1996 |
| WO | WO 96/40174 | 12/1996 |
| WO | 9915209 * | 4/1999 |

OTHER PUBLICATIONS

Official Action for A 1593/97 dated Apr. 9, 1997.
International Search Report for PCT/EP/05995, dated Apr. 26. 1999.
Bering, E.A. Jr., "Chemical, Clinical, and Immunological Studies on the Products of Human Plasma Fractionation", *J. Clin. Invest.*, vol. 23, 1944, pp. 586–590.
Gerendas, M., "Fibrin Products as Aids in Hemostasis and Wound Healing", pp. 227, K. Laki (ed.) Fibrinogen, M. Dekker, New York, 1968.
Redl, H. and Dinges, H.P., Med. Welt., vol. 36, 1985, pp. 769–776.

* cited by examiner

*Primary Examiner*—Kim M. Lewis
(74) *Attorney, Agent, or Firm*—Foley, Hoag & Eliot LLP

(57) ABSTRACT

The invention relates to a fibrin sponge comprising a residual moisture content of at least 3%, preferably of 3 to 35%, in particular 10 to 20%, and preferably containing a blood clotting activator or proactivator, a method of preparing this fibrin sponge as well as a kit for wound gluing which comprises the fibrin sponge and a component containing a blood clotting factor. The sponge according to the present invention is suitable for hemostasis, tissue adhesion and aiding wound healing.

42 Claims, No Drawings

FIBRIN SPONGE

The present invention relates to a fibrin sponge having a defined residual moisture, methods of its preparation, its use for hemostasis, tissue adhesion and supporting wound healing as well as a kit for its application.

In the prior art, the most varying hemostatic wound cover materials, also based on fibrin, e.g. fibrin sponges, fibrin membranes or fibrin gels, have been described and partially also used.

So far the opinion has prevailed that for hemostasis, a combination of fibrinogen and thrombin or corresponding prothrombin activators is necessary. Thus, e.g., fleece-like flat materials based on collagen comprising fibrinogen and thrombin (TachoComb®), flat materials comprising fibrinogen and activated factor X (AT 0 359 653, IMMUNO AG) or flat materials comprising fibrinogen and thrombin as a dry preparation (EP 0 748 633, IMMUNO AG) have been known from the prior art. Whereas the fleece-like flat materials based on fibrinogen and activated factor X are already soft and pliable, other flat materials require absolutely dry storage so as to preclude a premature reaction of the fibrinogen contained therein with the thrombin or with other blood clotting activators.

Bering E. A. jr. (J. Clin. Invest. Vol. 23, 1944, p. 586) discusses general developments in the field of fibrin foams and their use as hemostatic agents.

A survey of various materials based on fibrin, e.g. fibrin powders, fibrin films and fibrin foams, is e.g. given in Gerendas M. "Fibrin Products as aids in hemostasis and wound healing", pp. 277, in K. Laki (ed.) Fibrinogen, M. Dekker, New York, 1968.

Furthermore, fibrin foils or fibrin membranes, respectively, have been known from the prior art (cf. e.g. EP 0 485 210-A2). Such materials are extremely thin, non-absorbent and thus usable for hemostasis to a limited extent only. In contrast to fibrin sponges, these materials are compressed on purpose during their preparation, e.g. by the application of weights. Therefore, these materials are primarily characterized by their high density, as compared to foams.

The present invention has as its object to provide a means for hemostasis, tissue adhesion and the aiding of wound healing based on fibrin which, compared to conventional means, has a good, in particular an improved, efficacy, is simple to handle with a simultanous simple composition that allows for an inexpensive preparation, and which also has a broad field of application. Therebeyond, it should be possible to readily supply the fibrin material with other active and auxiliary substances.

According to the invention, this object is achieved in that a fibrin sponge having a residual moisture of at least 3%, preferably in the range of from 3 to 35%, in particular 10 to 20%, is provided which is storage stable. The water content or the residual moisture, respectively, preferably is adjusted such that the fibrin sponge has a soft and smooth consistency, thereby substantially improving its handling and efficacy.

From the prior art it has been known that dry preparations containing fibrin, which have a hard, brittle consistency, will become soft and smooth (pliable) by increasing their residual moisture. However, there has been a general prejudice as regards the stability of such protein preparations having an increased residual moisture, particularly if they contain a sensitive enzyme, such as thrombin, or another activator or proactivator of blood clotting.

It is not without reason that such sensitive protein preparations commonly are made stable by lyophilisation, a residual moisture of less than 3%, in most instances even of less than 1%, being attained.

Therefore, it has been suprising that a fibrin sponge preferably having a content of thrombin and an increased residual moisture or an increased water content nevertheless is storage stable.

By storage-stable according to the present invention, a fibrin sponge is understood which even after a storage of 6 months, generally, however, even after a storage of 2 or more years at room temperature is still extremely suitable for application, and the optionally present thrombin activity or blood clotting activator or proactivator activity remains substantially preserved. Preferably, more than 70% of the activity remain over a period of at least 6 months, preferably 2 or more years, at room temperature. Even at a temperature of 370° C. the fibrin sponge according to the invention having a residual moisture of 15% has been shown to be stable for at least 3 months, preferably more than 6 months, its thrombin activity being fully retained.

The preparation according to the invention particularly meets the manifold requirements made on a means for hemostasis, tissue adhesion and aiding wound healing, with the preparation according to the invention, properties such as

- a good and lasting efficacy, i.e. rapid hemostasis or adhesive effect, no secondary bleedings or late detachment of glued tissue parts,
- a good tolerance even with multiple applications (no sensitisation)
- complete resorption during the wound healing process,
- smooth and undisturbed wound healing,
- the greatest possible safety as regards the transmission of viral or other pathogens (such as, e.g., prions, the pathogens of bovine spongiform encephalitis, BSE),
- simple use as well as the already mentioned
- storage stability of the ready-to-use product can, e.g., be ensured.

Preferably, the fibrin sponge according to the invention is a fibrin fleece-like flat material or a fibrin foam having a low density and a high absorptive capacity.

According to the invention, by fibrin fleece-like flat material a fibrin sponge is to be understood which has a porous, in particular fine porous structure substantially not interspersed by air bubbles, as it might be obtained by lyophilising non-foamed fibrin clots according to the invention. By fibrin foam, on the other hand, a material is to be understood which is obtained by foaming a fibrinogen solution, admixing with a thrombin solution and lyophilising the thus obtained foamed fibrin clot. Foaming may also occur immediately after the addition of the thrombin.

The fibrin sponge according to the invention may also be used as such. It may essentially consist of fibrin and the thrombin required for producing the fibrin from fibrinogen, and surprisingly even this simple embodiment exhibits an excellent hemostatic and adhesive effect.

It may, however, be impregnated with further additives, preferably a blood clotting activator or proactivator. Such additives are preferably homogenously distributed in the preparation according to the invention.

The blood clotting activator or proactivator preferably is selected from the group consisting of thrombin, prothrombin, activated factor X, prothrombin complex, activated prothrombin complex, FEIBA, calcium ions and mixtures thereof.

In particular, additional thrombin may be incorporated into the preparation according to the present invention, preferably in an amount of between 1 and 300 U/cm$^3$, more preferably between 5 and 100 U/cm$^3$, most preferably between 10 and 50 U/cm$^3$.

Surprisingly, it has been found that the preparations according to the invention based on solid fibrin also with an additional content of thrombin are still stable over long periods of storage at refrigerator or room temperature and even at 37° C. (in an accelerated stability test). In particular, the thrombin activity contained is substantially maintained over long periods of time. The contained thrombin activity may, e.g. after extraction with 1 M NaCl solution, be determined according to methods known per se, e.g. with a chromogenic substrate (Th-1, Pentapharm).

In addition to substances, such as blood clotting activators or proactivators, the fibrin sponge according to the invention may also contain stabilizers, preservatives, antibiotics, therapeutic agents, antifibrinolytic agents, growth factors, further plasma proteins, enzymes, inhibitors or mixtures of such agents.

As stabilizers, preferably thrombin stabilizers, in particular polyoles, polysaccharides, polyalkylene glycols, amino acids or mixtures thereof, or substances stabilizing the water content, in particular polysaccharides or polyoles, are used. The use of sorbitol, glycerol, polyethylen glycol, polypropylene glycol, mono- or disaccharides, such as glucose or sucrose, or any sugar or amino acid which stabilizes the thrombin activity or the residual moisture, respectively, is preferred there.

Likewise, the desired softness of the preparation may be attained or improved by incorporating substances, e.g. hydro-stabilizing active substances, such as glycerol. After lyophilizing in the presence of such substances, increased residual moisture levels can be obtained.

A preferred antifibrinolytic agent is selected from the group consisting of aprotinin, aprotinin derivative, α-2-macroglobulin, α-2-plasmin inhibitor, α-1-plasmin inhibitor, plasminogen activator inhibitor, inhibitor or inactivator of activated protein C, a plasmin-binding substance, or mixtures of these substances. Also synthetic substances, in particular synthetic fibrinolysis inhibitors, e.g. ε-aminocaproic acid or tranexamic acid, may be used. Also non-plasmatic antifibrinolytics, of vegetable origin, e.g., may be used according to the invention.

Preferred growth factors are, e.g., cytokines. As further plasma proteins preferably albumin, factor XIII or fibronectin are provided.

Furthermore, also specific proenzymes, enzymes or enzyme inhibitors may be admixed with the fibrin sponge according to the invention, e.g. so as to regulate the absorption of the fibrin sponge in the body, i.e. either to accelerate or to inhibit it. Among these substances are, e.g., plasminogens, collagenase, plasminogen activators, plasminogen activator inhibitors, plasmin inhibitors or elastase inhibitors.

The preparations according to the invention as such already have a good absorptive capacity. Preferably, a slight amount of a tenside, such as Tween® 80 (polyoxyethylene sorbitan monooleate) is additionally incorporated, whereby the absorptive capacity of the preparation according to the invention may additionally be increased.

The preparation according to the invention thus is particularly characterized by the following properties:

It has a great softness or adaptability so that it can be applied to an unevenly formed wound surface without any problems. Furthermore, it has a high absorptive capacity, whereby the emerging blood can be taken up without any delay.

Preferably, the fibrin sponge according to the invention has a liquid absorption capacity of at least the 2-fold, preferably of more than the 4-fold, of its own weight.

In a preferred embodiment, the material has a homogenous distribution of its coagulation-promoting properties of such a level that the sucked-up blood clots in the preparation according to the invention within a few seconds, preferably within less than 30 seconds.

The present invention also relates to a method of preparing a fibrin sponge based on fibrin, which is characterized by the following steps:

preparing a fibrin clot by mixing fibrinogen and thrombin and incubating the mixture at a temperature, preferably at 20 to 37° C., for a period of time sufficient for the formation of the fibrin, clot and in particular to complete cross-linking of the fibrin, preferably 10 min to 24 h, (deep-freezing and) lyophilizing the fibrin clot, and adjusting a residual moisture of at least 3%, preferably 3 to 35%, in particular between 10 and 200%.

In a preferred embodiment, adjusting of the water content is effected during lyophilizing. The residual moisture may, however, also be adjusted to the desired level after lyophilisation by incubating in a humid chamber.

When producing a preparation according to the invention, preferably also a washing and/or incubating step is provided. By this, in particular soluble components, such as e.g. salts, can be removed, while the content of thrombin which is given on account of the preparation method surprisingly is retained to a large extent.

Washing may be effected with distilled water, yet also solutions containing further active substances or additives may be used. Thus it is possible to purposefully adjust or vary the composition of the final product.

In particular it has been found that the thrombin contained in the fibrin clot practically cannot be eluted by washing with an isotonic saline solution. For instance, after washing for 4 hours with the 10-fold volume of isotonic saline solution, only approximately 4% of the total thrombin are found in the washing solution. On the other hand, other plasma proteins, such as, e.g. albumin, are eluted comparatively rapidly under the same conditions (approximately 25% in 4 hours, approximately 50% in 8 hours).

Finally, the as such surprisingly high stability of the blood clotting activator or proactivator, respectively, which preferably is homogenously distributed in the preparation according to the invention, can still be further increased by stabilizers known per se, such as, e.g., sugars, sugar alcohols, polyoles, amino acids, etc., or mixtures thereof.

In a further preferred embodiment, in the course of its preparation, the fibrin sponge is washed and/or impregnated with further substances, as has already been mentioned earlier. Preferably, the fibrin clot is impregnated prior to lyophilisation. It is, however, also possible to effect washing or incubating, respectively, after lyophilisation, this then being followed by a further lyophilisation step.

The fibrin foam can be prepared by foaming the fibrinogen solution before or immediately after mixing with thrombin, yet before clotting occurs. All the means common in the prior art may be utilized for this foaming. For instance, these may be chemical, physical and/or mechanical means or methods. Gases may be introduced or generated, in particular air is introduced by intesive, mechanical stirring (Ultraturrax treatment or the like). As an example of a physical method, the application of a vacuum may be mentioned.

Furthermore, however, it has been found that in contrast to the hitherto described methods of preparing fibrin sponges, it is not absolutely necessary to foam the fibrinogen solution or the fibrinogen thrombin mixture before the onset of clotting.

In contrast to the hitherto described methods of preparing fibrin sponges, particularly fine-porous and absorbent preparations are produced after lyophilisation without substantial shrinkage from fibrin clots that have been prepared without foaming.

Before freezing and lyophilizing, the fibrin clot preferably has a relatively low salt content or a low ionic strength, respectively, preferably less than 0.15, preferably it is substantially free from salts.

Avoiding foaming substantially simplifies and facilitates the preparation method, particularly if the latter is to be carried out under sterile conditions.

In a further preferred embodiment, the fibrin sponge, i.e. in particular the fibrin flat material or the fibrin foam, is cut after its respective preparation. Preferably, it is cut such that after cutting, the cut area which then can be used as a wound cover is as large as possible. Surprisingly it has been found that the absorptive capacity of these cut areas is even higher than that of the uncut, so-to-speak "native", surfaces immediately after lyophilisation.

The good tolerance even after multiple application, in particular the avoidance of allergic reactions, is preferably attained by the exclusive use of human proteins as well as by avoiding methods, e.g. sterilizing methods, by which the proteins may become denatured (such as, e.g., by γ-irradiation)

In a particularly simple embodiment, the preparation of the wound cover according to the invention is effected from a sterile starting material, by maintaining sterile conditions up to the final product.

Preferably, the preparation according to the invention is prepared from human plasma protein fractions which have been treated according to suitable virus inactivation methods for sensitive plasma proteins.

The inactivation treatment preferably is ensured by a tenside and/or heat treatment, e.g. by a heat treatment in the solid state, in particular a vapour treatment according to EP 0 159 311, EP 0 519 901 or EP 0 674 531.

In one preferred embodiment the heat treatment is carried out as a vapour heat treatment with a residual water content between 6 and 15%, preferably about 12%. When thrombin is present in the sponge it was surprisingly found that even under these conditions nearly all of the thrombin activity was maintained.

Further steps for inactivating viruses also comprise the treatment with chemical or chemical/physical methods, e.g. with chaotropic substances according to WO 94/13 329, DE 44 34 538 or EP 0 131 740 (solvents) or photoinactivation.

Preferably, two independent virus inactivation methods are carried out.

Nanofiltration also constitutes a preferred method for depleting viruses within the scope of the present invention.

A further possibility of increasing the virus safety consists in initially starting the preparation exclusively from—to the greatest possible extent—virus-safe starting substances and then to exclude all risks of contamination in the course of the preparation process. The greatest possible safety in terms of the transmission of viral or other pathogens in the preparation from human plasma is additionally ensured by carefully selecting and monitoring the plasma donors, testing the starting plasma for pathogenic viruses (preferably single donation testing), in particular by means of PCR methods.

Yet basically, the preparation according to the invention may also be prepared from recombinant or transgenic material, wherein the necessary safety measures also have to be met.

Preferably, the preparation is effected under sterile conditions, starting from sterile intermediate products (sterile-filtered solutions) up to the sterile packed final product, so that a subsequent sterilisation in the final container, such as, e.g., by γ-irradiation, is no longer necessary.

The complete absorption during the wound healing process as well as the smooth and undisturbed wound healing are attained by using fibrin and optionally further plasma proteins, such as, e.g., fibronectin, as the matrix, the formation of fibrin preferably taking place at approximately physiologic ionic strength, at approximately physiologic pH and in the presence of factor XIII, so that a cross-linked fibrin clot having a physiological fibrin structure is obtained which is essential for the germination of fibroblasts and thus for a rapid and smooth wound healing (cf. also Redl at al. Med. Welt, 36, pp. 769–776, 1985).

The length and width of the fibrin sponge according to the invention can be chosen freely depending on the type of use. Its thickness is preferably in a practicable range of between 1 and 20 mm, depending on the indication, thicknesses between 3 and 15 or between 5 and 10 mm, respectively, being preferred.

The fibrin sponge according to the invention may also be present as a combination with other materials.

In a specific embodiment the sponge is made up of several layers so that a multilayered material is formed. Preferably a least one layer has hemostatic properties. The layers may be built up by the same material or they may differ in material and/or their composition.

The sponge material may be characterized by the specific weight of the material or each layer. In a preferred embodiment the specific weight is between 0.005 and 0.15 g/cm$^3$, more preferably 0.01 to 0.09 g/cm$^3$, most preferred 0.02 to 0.05 g/cm$^3$.

In another preferred embodiment the layers are composed of the same material but differing in their physical properties like e.g. their specific weight. By varying the physical properties of the layers, a sponge may be obtained which is characterized in that one side of this sponge is smooth, with a high absorptive capacity, while the other side of the sponge is more compact and tight. Another way of varying the properties of the different layers can be achieved by varying the amount or concentration of the substances forming the layer or of those substances with which each layer is impregnated. So for example, the concentration of thrombin in the different layers may be different.

The use of the fibrin foam, e.g., will be such that it is applied onto the bleeding wound and is slightly pressed thereto for a short period of time (approximately 30 seconds). The sponge sucks up the blood very rapidly, the sucked up blood clotting within the sponge. Thereby a tight anchoring of the fibrin sponge on the wound surface will be attained, which at last is the basis of its hemostatic and adhesive effect.

The preparation may also be used as a so-called dry adhesive, preferably as a relatively thin sponge. To glue together two (soft) bleeding tissue parts, a suitable piece of the "dry adhesive" is applied to a wound surface, and subsequently the second wound surface (the second tissue part) is adapted and shortly pressed thereto.

The medical field of indication for the fibrin sponge according to the invention is quite large. Not only can the sponge be used to stop a seeping hemorrhage, it may also be used for stopping a hemorrhage in case of very large bleeding areas with a high blood pressure. The following internal and external surgical procedures may successfully be carried out by using the fibrin sponge according to the invention: general surgery, e.g. surgery on parenchymatous organs (liver, kidney, spleen etc.), cardiovascular surgery, thorax surgery, grafting surgery, orthopedic surgery, surgical operations in the fields of bone surgery and plastic surgery, ear, nose and throat surgery, operations in the field of neurosurgery, operations in the urologic and gynecologic tracts, as well as generally for hemostasis as well as for treating conventional wounds.

According to a further aspect of the present invention, also a kit for gluing wounds is provided, which is characterized in that it comprises a fibrin sponge according to the invention and a component containing a blood clotting factor.

Preferably, this blood clotting factor is fibrinogen, factor XIII, fibronectin, thrombin or mixtures of these factors, a fibrinogen component preferably in storage-stable form, such as a commercially available product of a tissue adhesive based on fibrinogen being particularly preferred.

The sponge according to the present invention may also be useful as a biological support for cell cultures, especially for mammalian cells like e.g. keratinocytes, epithelial cells, epidermal cells, fibroblasts, chondrocytes or the like.

Therefore, according to the present invention also a kit is provided comprising a fibrin sponge according to the present invention in sterile form for use as a biological support for cell cultures.

Further additives like e.g. antibiotics, various amino acids and/or various growth factors may be present within the sponge or may be added later to the used medium.

In using the fibrin sponge according to the present invention as a support for growing cells, it is possible to form replacements of tissue like e.g. skin, bone, cartilage and/or nerves, respectively.

The invention will be explained in more detail by the following example without, however, restricting it thereto:

EXAMPLE 1

Fibrin fleece-like flat material of cross-linked fibrin having a (relatively low) content of thrombin.

1.1 Preparation

A commercially available tissue adhesive preparation, virus inactivated by vapour treatment and lyophilized (Tissucol®, IMMUNO AG) served as the starting material for preparing a fibrinogen solution having a content of factor XIII and fibronectin. The preparation was dissolved according to the producer's instructions with an aqueous aprotinin solution (3000 KIU/ml) and further diluted 1:4 with distilled H$_2$O to yield a fibrinogen concentration of approximately 20 mg/ml. 20 ml of this solution were rapidly mixed with 20 ml of a thrombin-CaCl$_2$ solution (human thrombin, approximately 10 U/ml 5 mM CaCl$_2$) and poured into a Petri dish (ID=8.4 cm), at first allowed to stand undisturbed at room temperature for approximately 30 min and then incubated for approximately 16 further hours in a humid chamber at 37° C. The clot in form of a round disc having a thickness of approximately 7 mm was then deep-frozen and lyophilized. The lyophilisate formed (fleece-like flat material) had a light, fine-porous appearance and substantially retained the form of the clot prior to lyophilisation. Yet the material was still too brittle for an optimum application. To improve the desired softness and pliability, the flat material was incubated for approximately 3 h in a humid chamber at room temperature, whereby a soft, adaptable and highly absorbent material was obtained.

| 1.2: Analysis, in vitro testings: | |
| --- | --- |
| Residual moisture: | approximately 15% |
| Pliability: | >90° at a mean radius of curvature corresponding to half the layer thickness |
| Fibrin cross-linking: | γ-chains: 100% |
| | α-chains: approximately 80% |
| Thrombin content: | determination after extraction with 1 M NaCl: 1.4 U/cm$^3$ |
| Water absorption capacity: | approximately the 6-fold of its own weight |
| Water absorption rate: | a drop of water (50 μl) placed onto the surface of the flat material is completely sucked up in approximately 25 s |

(on cut areas of the flat material under otherwise equal conditions water is absorbed practically immediately, i.e. in less than 5 s).

1.3 Efficacy

The adhesive and hemostatic effect of the preparation prepared according to 1.1 was tested in the so-called kidney pole resection model on a rabbit.

For this, a kidney was exposed on the test animal under anesthesia with kedamin and xylazin (after-dosing with pentobarbital), and the kidney pole was removed with the scalpel. A circular area bleeding with uniform intensity and having a diameter of approximately 1 to 1.5 cm is formed. The test preparation is applied onto the bleeding area, slightly pressed thereto by means of the finger for exactly 30 s and then released. Adhesion of the preparation is observed, and the time until complete hemostasis is measured. Possibly seeped out blood is taken up with gauze swabs, and the loss of blood is calorimetrically determined after extraction with ammonia from the test material and the gauze swabs.

Testing with the preparation obtained according to 1.1. was performed on two rabbits.

Results

In both instances, the preparation adhered well on the intensively bleeding surface, and complete hemostasis was attained practically immediately (in less than 30 s). No after bleedings occurred during a secondary observation period of 1 h.

Total blood loss (sucked up in the test material, no other seeped out blood) amounted to 0.10 and 0.18 ml, respectively.

In comparison thereto, with conventional hemostasis by means auf gauze the blood loss in this model is approximately 5 ml with a bleeding time of 3 min, and approximately 27 ml with a bleeding time of 9 min without any treatment.

The substantially improved efficacy of the preparation obtained according to 1.1 as compared to conventional means thus has been impressively demonstrated.

What is claimed is:

1. A storage-stable fibrin sponge comprising a residual moisture of at least 10%.

2. The storage-stable fibrin sponge as set forth in claim 1, wherein said residual moisture ranges from 10% to 35%.

3. The storage-stable fibrin sponge as set forth in claim 1, wherein said residual moisture ranges from 10 to 20%.

4. The storage-stable fibrin sponge as set forth in claim 1, further comprising a blood clotting activator or proactivator.

5. The storage-stable fibrin sponge as set forth in claim 4, wherein said blood clotting activator or proactivator is selected from the group consisting of thrombin, prothrombin, activated factor X, activated prothrombin complex, FEIBA, calcium ions and mixtures thereof.

6. The storage-stable fibrin sponge as set forth in claim 5, wherein said blood clotting activator is thrombin, said thrombin being comprised in an amount of from 1 to 300 U/cm$^3$.

7. The storage-stable fibrin sponge as set forth in claim 5, wherein said thrombin is comprised in an amount of from 5 to 100 U/cm$^3$.

8. The storage-stable fibrin sponge as set forth in claim 5, wherein said thrombin is comprised in an amount of from 10 to 50 U/cm3.

9. The storage-stable fibrin sponge as set forth in claim 1, further comprising a member selected from the group consisting of: stabilizers, preservatives, antibiotics, therapeutic agents, antifibrinolytic agents, growth factors, further plasma proteins, enzymes, inhibitors and mixtures of these agents.

10. The storage-stable fibrin sponge as set forth in claim 1, said fibrin sponge having a liquid absorption capacity of at least the 2-fold of its own weight.

11. The storage-stable fibrin sponge as set forth in claim 1, wherein said fibrin sponge has a liquid absorption capacity which is 4-fold of its own weight.

12. The storage-stable fibrin sponge as set forth in claim 1, wherein said fibrin sponge is virus inactivated.

13. The storage-stable fibrin sponge as set forth in claim 12, wherein said virus inactivation has been effected in two independent virus inactivation steps.

14. The storage-stable fibrin sponge as set forth in claim 1, said fibrin sponge being free from elutable plasma proteins.

15. The storage-stable fibrin sponge as set forth in claim 1, said fibrin sponge being free from elutable thrombin.

16. The storage-stable fibrin sponge as set forth in claim 1, said fibrin sponge having been prepared from virus-safe starting substances.

17. The storage-stable fibrin sponge as set forth in claim 1, said fibrin sponge being provided in an aseptic package and in ready-to-use form.

18. The storage-stable fibrin sponge as set forth in claim 1, said fibrin sponge having a thickness of at least 1 mm.

19. The storage-stable fibrin sponge as set forth in claim 1, said fibrin sponge having a thickness of between 5 and 10 mm.

20. The storage-stable fibrin sponge as set forth in claim 1, said fibrin sponge being multilayered.

21. The storage-stable fibrin sponge as set forth in claim 20, wherein at least one layer of said multilayered fibrin sponge has hemostatic properties.

22. The storage-stable fibrin sponge as set forth in claim 1, said fibrin sponge having a specific weight of between 0.005 and 0.15 g/cm3.

23. The storage-stable fibrin sponge as set forth in claim 22, wherein said specific weight of said fibrin sponge ranges between 0.01 and 0.09 g/cm3.

24. The storage-stable fibrin sponge as set forth in claim 22, wherein said specific weight of said fibrin sponge ranges between 0.02 and 0.05 g/cm3.

25. A kit for wound coverage, said kit comprising a storage-stable fibrin sponge having a residual moisture of at least 10% and a component containing a blood clotting factor.

26. The kit as set forth in claim 25, wherein said blood clotting factor is selected from the group consisting of fibrinogen, factor XIII, fibronectin, thrombin and mixtures of said factors.

27. A method of preparing a fibrin sponge, said method comprising preparing a fibrin clot by mixing a fibrinogen solution with a thrombin solution and incubating the resulting mixed solution at a certain temperature for a period of time sufficient for formation of said fibrin clot, b) deep-freezing and lyophilizing said fibrin clot, and c) adjusting a residual moisture in said fibrin clot to at least 10%.

28. A method as set forth in claim 27, wherein said fibrinogen solution contains factor XIII, and said thrombin solution contains Ca$^2+$ ions, and said temperature for incubating ranges between 20 and 37° C., and incubating of said mixed solution is carried out for a period of time sufficient for cross-linking of said fibrin formed, and wherein a residual moisture of from 10% to 35% is adjusted.

29. The method as set forth in claim 27, wherein said incubating of said mixed solution is carried out for a period of time of from 10 min to 24 h, and wherein a residual moisture of from 10 to 20% is adjusted.

30. The method as set forth in claim 27, further comprising packing said fibrin sponge in a suitable container.

31. The method as set forth in claim 30, wherein said container is at least one of air-tight and water-tight.

32. The method as set forth in claim 27, wherein at least one of said fibrinogen solution and said thrombin solution further comprises at least one of another plasma protein, another active substance and an auxiliary agent.

33. The method as set forth in claim 32, further comprising at least one of washing said fibrin clot with water or with an aqueous solution and incubating said fibrin clot with an additional solution, said additional solution containing at least one member selected from the group consisting of thrombin, another plasma protein and another active substance.

34. The method as set forth in claim 33, wherein said at least one of washing and incubating with said further solution containing said at least one of thrombin, an additional plasma protein and an auxiliary agent is effected after lyophilizing, followed by another deep-freezing and lyophilizing step.

35. The method as set forth in claim 32, wherein said additional plasma protein is selected from the group consisting of fibronectin, a fibrinolysis inhibitor, plasminogen and albumin, and wherein said additional active substance is selected from the group consisting of a non-plasmatic and synthetic fibrinolysis inhibitor, an antibiotic and a growth hormone.

36. The method as set forth in claim 32, wherein said auxiliary agent is selected from the group consisting of sugar, sugar alcohol, polyol, amino acid, tenside, plasticizer and a moistening agent.

37. The method as set forth in claim 32, wherein said auxiliary agent is glycerol.

38. The method as set forth in claim 27, further comprising foaming said fibrinogen solution or a mixture of said fibrinogen solution with said thrombin solution before said formation of said fibrin clot.

39. The method as set forth in claim 27, further comprising cutting said fibrin clot after said fibrin clot has been lyophilized.

40. The method as set forth in claim 27, wherein said preparing of said fibrin clot is effected from a sterile starting material, further comprising maintaining sterile conditions throughout said method.

41. A method of treating a patient suffering from wounds and hemorrhages, said method comprising applying to said patient a fibrin sponge having a residual moisture of at least 10%, for at least one of hemostasis, tissue adhesion, cell culture supported healing and wound healing.

42. A kit comprising a storage-stable fibrin sponge having a residual moisture of at least 10% is sterile form for use as a biological support for cell cultures.

* * * * *